United States Patent [19]
Katzberg et al.

[11] Patent Number: 6,122,540
[45] Date of Patent: *Sep. 19, 2000

[54] NONINVASIVE MEASUREMENT OF RENAL HEMODYNAMIC FUNCTIONS USING MAGNETIC RESONANCE IMAGING

[75] Inventors: Richard W. Katzberg, Carmichael, Calif.; Charles L. Dumoulin, Ballston Lake, N.Y.

[73] Assignee: The Regents of the University of California, Oakland, Calif.

[*] Notice: Under 35 U.S.C. 154(b), the term of this patent shall be extended for 658 days.

[21] Appl. No.: 08/497,024

[22] Filed: Jun. 30, 1995

Related U.S. Application Data

[63] Continuation of application No. 08/257,011, Jun. 8, 1994, abandoned.

[51] Int. Cl.⁷ ................................................. A61B 5/055
[52] U.S. Cl. ........................................... 600/419; 600/420
[58] Field of Search ................................ 600/419, 420, 600/410

[56] References Cited

U.S. PATENT DOCUMENTS

| | | | |
|---|---|---|---|
| 4,796,635 | 1/1989 | Dumoulin | 128/653 |
| 4,804,529 | 2/1989 | Bardy et al. | 424/9 |
| 4,985,233 | 1/1991 | Klaveness et al. | 424/9 |
| 5,055,288 | 10/1991 | Lewis et al. | 424/9 |
| 5,078,986 | 1/1992 | Bosworth | 424/9 |
| 5,100,646 | 3/1992 | Choyke et al. | 424/9 |
| 5,190,744 | 3/1993 | Rocklage et al. | 424/9 |
| 5,204,625 | 4/1993 | Cline et al. | 324/306 |
| 5,335,660 | 8/1994 | Dumoulin | 128/653.3 |

OTHER PUBLICATIONS

Katzberg et al., "Mechanism of the Renal Response to Contrast Medium in Dogs—Decrease in Renal Function due to Hypertonicity," *Investigative Radiology*, 18(1):74–80 (1983).

Katzberg et al., "A Comparison of Clearance and Arteriovenous Extraction Technique for Measurements of Renal Hemodynamic Functions," *Investigative Radiology*, 21(12):910–916 (1986).

Katzberg et al., "Effects of Contrast Media on Renal Function and Subcellular Morphology in the Dog," *Investigative Radiology*, 21(1):64–70 (1986).

*Primary Examiner*—Ruth S. Smith
*Attorney, Agent, or Firm*—Townsend and Townsend and Crew LLP

[57] ABSTRACT

A magnetic resonance imaging method of in-vivo measurement for renal hemodynamic functions by obtaining renal function images in the presence of an intravascular contrast agent with a modified inversion recovery pulse sequence imaging technique, determining the renal artery and renal vein blood longitudinal relaxation times from the data derived from the images and employing these times to arrive at the filtration fraction.

3 Claims, 1 Drawing Sheet

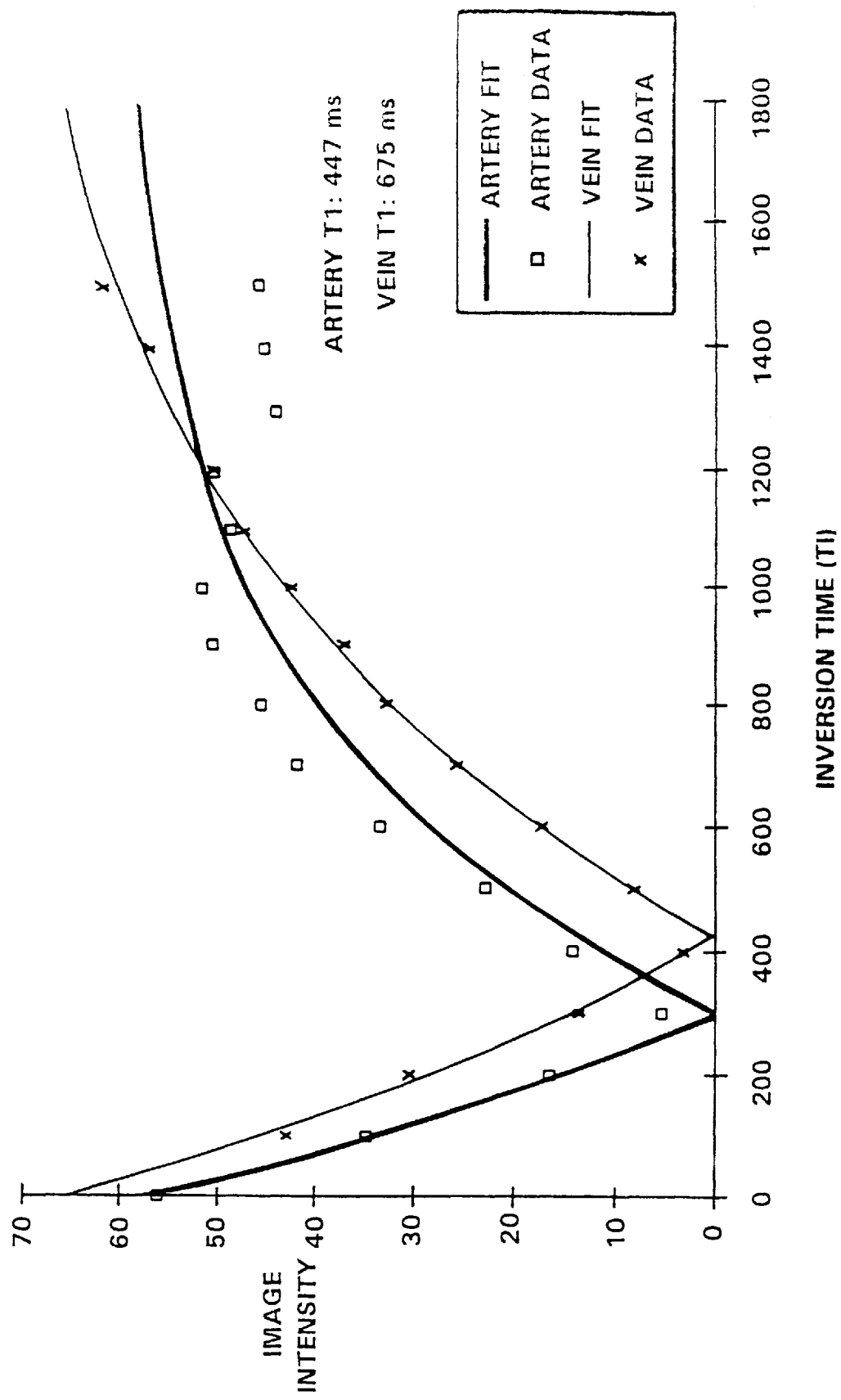

NONINVASIVE MEASUREMENT OF RENAL HEMODYNAMIC FUNCTIONS USING MAGNETIC RESONANCE IMAGING

This is a continuation of application Ser. No. 08/257,011 filed Jun. 8. 1994 now abandoned.

FIELD OF THE INVENTION

The field of the invention is the noninvasive determination of renal hemodynamic functions in the presence of an intravascular contrast agent and using magnetic resonance imaging techniques.

BACKGROUND OF THE INVENTION

Current clinical techniques used to determine glomerular filtration rate (GFR) are based on the concept of clearance. Under normal steady-state conditions, the daily production of creatinine is equal to the daily excretion of creatinine, regulating serum creatinine within a narrow range. Thus, clinicians frequently use serum creatinine concentration alone as an estimate of the GFR. However, this technique has limited accuracy and the presence of unllateral kidney disease is usually not detectable. Even moderate degrees of renal insufficiency can be masked by a serum creatinine concentration falling within the normal range. Thus, a reduction in GFR of up to 50% may occur in conjunction with a normal serum creatinine concentration.

Direct measurement of clearance frequently provides a better indicator of renal status than serum creatinine, particularly in early stages of renal disease. If the clinical suspicion of renal dysfunction is high, a more exact determination of GFR by endogenous creatinine clearance will provide a more accurate assessment of renal function. The use of these conventional clearance methods requires the collection of multiple urine and blood samples and, in theory, requires steady-state conditions to approximate GFR. Renal clearances can also be measured during maintenance of a constant concentration of inulin in the plasma. Inulin has been established as the ideal reference material because as the volume of distribution of the marker remains constant with constant infusion, it is freely filtered and is neither reabsorbed nor secreted. Other exoganous substances have been used as markers for the evaluation of renal clearance and include chelating compounds such as DTPA (diethylene triamine pentaacetic acid), exogenous creatinine, sodium lothalamate and vitamin B12.

The disadvantages of conventional clearance techniques are that they require timed urine collections which do not accurately reflect changing urine flow rates, acute changes in renal functions, variations in residual bladder volume, changes in reabsorption of the marker at markedly reduced urine flows, variations in protein binding of the marker and plasma, presence of drugs that compete with the marker for excretion, degradation or synthesis of the marker in the kidney and variation of clearance rates with a marker concentration that exceeds a reabsorptive or secretory transport maximum. Conventional clearance techniques requiring urine collections are not feasible in conditions of partial or total cessation of urine flow. This can occur in dehydrated states or during obstructive uropathy.

Some of the limitations of conventional clearance techniques can be overcome with a more invasive method using the plasma extraction ratio (filtration fraction) of inulin, creatinine or DTPA compounds multiplied by the plasma flow. The arteriovenous determination of glomerular filtration rate (GFR) is the product of the filtration fraction (FF) and renal plasma flow (RPF):

$$GFR = FF \times RPF \quad (1)$$

Filtration fraction can be expressed as:

$$FF = \frac{Ca - Cv}{Ca} \quad (2)$$

where Ca is the contrast medium concentration in the renal artery and Cv is the contrast concentration in the renal vein. This measure of renal function encompasses both the extraction efficiency of the kidney and the amount of blood being filtered. It is a simple and rapid determination of single kidney function that is independent of timed urine collections.

Magnetic resonance measurement of blood flow has been demonstrated using a phase sensitive method. Magnetic resonance has also been demonstrated as a method to measure renal clearance using relaxation measurements in in-vitro serum and urine samples.

BRIEF DESCRIPTION OF THE INVENTION

The invention relates to in-vivo measurement of filtration fraction using magnetic resonance imaging (MRI) techniques with a modified inversion recovery pulse sequence. The disclosed technique permits the acquisition simultaneously of renal plasma flow and filtration fraction following an intravenous administration of a standard clinical dose of Gadolinium DTPA.

The application FIGURE illustrates experimental data with curve fits.

DETAILED DESCRIPTION OF THE INVENTION

The glomerular filtration rate is used to assess renal function. Accurate determinations of the glomerular filtration rate assist in determining renal health and injury.

Gadolinium-diethylene triamine pentaacetic acid (Gd-DTPA) and other chelated Gadolinium compounds are contrast agents which are widely used to enhance the appearance of pathologic lesions in magnetic resonance imaging, These compounds are biologically inert and are fully excreted through the kidneys like inulin. The Gadolinium atom at the center of each molecule has five unpaired electrons which creates a relatively strong paramagnetic moment. Since each Gd-DTPA molecule is tumbling rapidly, the paramagnetic moment modulates the local magnetic field of the neighboring water molecules and decreases their longitudinal relaxation time, $T_1$. Within the concentration commonly employed for the use of Gd-DTPA, the $T_1$ is linearly related to Gd-DTPA plasma concentration. The relaxation time observed for a collection of water molecules in the presence of a given concentration, C, of Gd-DTPA can be expressed as $$\frac{1}{T_1(\text{observed})} = \frac{1}{T_1(Gd=0)} + \frac{C}{RGdT_1(Gd=R)} \quad (3)$$

where $T_1(Gd=O)$ is the $T_1$ of blood in the absence of Gd-DTPA and $T_1(Gd=R)$ is the $T_1$ of blood in the presence of a reference concentration, RGd, of Gd-DTPA.

Rearranging the terms of the equation (3) results in $$C = RGdT_1(Gd = R)\left[\frac{1}{T_1(\text{observed})} - \frac{1}{T_1(Gd = 0)}\right] \quad (4)$$

Substituting equation (4) into equation (2) for filtration fraction FF, where Ca is derived from the observed $T_1$ in the arterial blood and Cv is derived from the observed $T_1$ in the venous blood, $$FF = \frac{T_1V - T_1A}{T_1B - T_1V}\left[\frac{T_1B}{T_1V}\right] \quad (5)$$

Where $T_1B$ is the $T_1$ of blood in the absence of Gd-DTPA, i.e., $T_1(Gd=O)$, $T_1A$ is the $T_1$ of the arterial blood, and $T_1V$ is the $T_1$ of the venous blood.

Renal function images are obtained with a modified inversion recovery MRI pulse sequence to measure the $T_1$ of moving blood. The pulse sequence comprises a non-spatially selective 180-degree inversion RF pulse followed by a series of 90-degree flip angle detection pulses. The 90-degree flip angle detection pulses are used to record the recovery of longitudinal spin magnetization in an image plane intersecting the renal artery and vein. Recovery rate is measured in each vessel and the $T_1$ of blood is determined.

The 180-degree inversion pulse is non-selective. Its purpose is to invert the z-component of magnetization of all spins everywhere in the body. All spins that are in the sensitive volume of the body coil are inverted. The 180-degree inversion pulse is not being used as a spin-echo pulse. It is triggered in synchronization with the subject's heart beat.

Each R-R electrocardiogram interval of the full sequence acquires a single phase encode step for 16 images. To create the image, 128 phase encode steps are needed, so 128 heart beats are used. These Images are obtained at the same spatial location and orientation.

Each of the 16 images has a unique and fixed inversion time TI after the 180-degree inversion pulse. After the inversion pulse, the longitudinal magnetization mz recovers exponentially to its equilibrium value. A change of the z-component with magnetization is identical in each TR interval (a time period equal to the interval between 180-degree inversion pulses), so an image can be created by interrogating the same recovery curve 128 times, for 128 phase steps.

In a determination of $T_1$ from a representative subject, 16 MR images were acquired. The first image was acquired with a TI of O, a few milliseconds after the 180-degree inversion pulse. The longitudinal magnetization mz is maximum negative at that time. Subsequent images were obtained at 100 millisecond intervals, thus the TI of each subsequent image is 100 milliseconds longer then the TI at the preceding image. Each successive image shows an increasing mz, starting from -mz, crossing through zero to the recovered mz state. The application figure shows a plot of image intensity versus TI for 16 images. At TI of about 300 milliseconds, the arterial blood has recovered to the null point and at TI of about 400 milliseconds, the venous blood has reached the null point. As can be observed, arterial blood recovers more rapidly than venous blood. At a TI of about 800 milliseconds, both the arterial blood and venous blood have recovered their longitudinal magnetization mz. The data is fit to exponential recovery curves to derive the $T_1$ values and standard error estimates. Using these $T_1$ values and the $T_1$ value for blood in equation (5) provides the filtration fraction FF. Multiplying FF by the renal plasma flow, derived from measured blood flow, provides the GFR.

Four subjects without renal disease, to be evaluated by contrast brain MR imaging, were assessed. Their age range was 21 to 65 years, there were three men and one woman, and their left renal arteries were studied. A 1.5 Telsa MR imaging scanner was used with a 5.5×11 inch receive only lumbar spine surface coil, 0.2 mmol/kg Gd-DTPA was injected and data collection for $T_1$ values began 20 to 30 minutes after contrast and brain imaging. The scan protocol has a 2 minute acquisition time for each $T_1$ measure. Table 1 shows the FF values obtained.

TABLE 1

Filtration Fraction Using Post-Gd Renal Artery-$T_1$

| | | Post-Gd | | |
|---|---|---|---|---|
| Case | Pre-Gd IVC ($T_1$ In msec) | Renal artery ($T_1$ in msec) | Renal vein ($T_1$ in msec) | FF (%) |
| 1 | 1,200 ± 15 | 430 ± 23 | 611 ± 52 | 46 ± 11 |
| 2 | 1,005 ± 21 | 469 ± 11 | 684 ± 52 | 57 ± 3 |
| 3 | 1,200 ± 15 | 343 ± 9 | 454 ± 12 | 34 ± 5 |
| 4 | 1,137 ± 16 | 470 ± 14 | 537 ± 12 | 21 ± 6 |

FF: filtration factor; IVC; inferior vena cava.

In addition, flow-encoding pulses can be used to induce phase shifts proportional to velocity. These phase shifts, as those skilled in the art will appreciate, can be used to measure blood flow. Moreover, the FF values and blood flow can be measured in the same scan.

The described technique provides the ability to acquire simultaneously RPF and FF following the intravenous administration of a standard clinical dose, or a dose of 0.1 mmol/kg–1.5 mmol/kg, of Gd-DTPA. This permits an extremely rapid method for assessing renal hemodynamic functions in each kidney and an anatomic evaluation. Measuring rapid transient responses in renal hemodynamic functions yields useful information that may be obscured by steady-state methods, is independent of timed urinary collections, and allows in the same examination single kidney assessments with detailed renal anatomy.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method of measuring renal function in a living subject comprising the steps of:
   a) obtaining a longitudinal spin relaxation time of said subject's blood without any added contrast agents, $T_1B$;
   b) injecting a longitudinal spin relaxation time contrast agent into said subject's blood shortening the longitudinal spin relaxation time of said blood;
   c) measuring a longitudinal spin relaxation time of pre-filtered blood, $T_1A$, prefiltered blood being blood on its way into the kidney, with magnetic resonance (MR) techniques, subsequent to injecting the contrast agent;
   d) measuring a longitudinal spin relaxation time of post-filtered blood, $T_1V$, post-filtered blood being blood on its way out of the kidney, with magnetic resonance (MR) techniques, subsequent to injecting the contrast agent; and e) calculating a filtration fraction, FF, from $T_1A$, $T_1B$, and $T_1V$ indicating the fraction of contrast agent filtered from said subject's blood.

2. The method of measuring renal function of claim 1, wherein the glomerular filtration rate, GFR, is calculated from filtration fractions, FF, and the renal plasma flow, RPF, according to $$GFR = FF \cdot RPF.$$

3. The method of claim 1, wherein the filtration fraction, FF, is determined according to:

$$FF = \frac{T_{1V} - T_{1A}}{T_{1B} - T_{1A}} \left[ \frac{T_{1B}}{T_{1V}} \right].$$

* * * * *